United States Patent [19]

Slater et al.

[11] Patent Number: 4,710,352

[45] Date of Patent: Dec. 1, 1987

[54] SIMPLIFIED TEST ELEMENT ADVANCING MECHANISM HAVING POSITIVE ENGAGEMENT WITH ELEMENT

[75] Inventors: Daniel A. Slater; William A. Meredith; Mark J. Devaney, all of Rochester, N.Y.

[73] Assignee: Eastman Kodak Company, Rochester, N.Y.

[21] Appl. No.: 777,985

[22] Filed: Sep. 20, 1985

[51] Int. Cl.$^4$ .......................................... G01N 35/00
[52] U.S. Cl. .................... 422/63; 198/465.1; 198/748; 198/803.01; 422/65; 436/46
[58] Field of Search .................. 198/465.1, 465.2, 748, 198/803.01; 436/46, 47; 422/65, 67, 73, 63

[56] References Cited

U.S. PATENT DOCUMENTS

| | | | |
|---|---|---|---|
| 3,104,768 | 9/1963 | Bassett | 198/748 |
| 3,655,025 | 4/1972 | Wilkin | 198/748 |
| 3,708,264 | 1/1973 | Jottier | 422/65 |
| 4,152,390 | 5/1979 | Nosco et al. | 422/65 |
| 4,219,529 | 8/1980 | Tersteeg et al. | 422/65 |
| 4,269,803 | 5/1981 | Jessop | 422/65 |
| 4,378,872 | 4/1983 | Brown | 198/748 |
| 4,424,191 | 1/1984 | Jakubowicz | 422/65 |
| 4,430,299 | 2/1984 | Horne | 422/67 |

FOREIGN PATENT DOCUMENTS 55-71951  5/1980  Japan ................................. 422/65

Primary Examiner—Michael S. Marcus
Attorney, Agent, or Firm—Dana M. Schmidt

[57] ABSTRACT

There is disclosed a test element advancing mechanism for use in an analyzer to move such test element from station to station, and a method of doing the same. The mechanism features a support surface over which the test elements move in a predetermined direction, a test element mover for engaging and moving the test elements, means for reciprocating the mover along a surface disposed to one side of the support surface, a portion of said mover being constructed to engage the reciprocating means, and means for pivoting the mover about an axis that extends parallel to the movement direction so that the engaging means are moved into or out of contact with such test elements. The test element mover includes a lever arm emanating from one side of the reciprocating means engaging portion, constructed to interact with the pivoting means. The mover also includes test element engaging means projecting from a side of the reciprocating means engaging portion that is opposite to the side from which projects the lever arm of the mover, for engaging the test elements.

9 Claims, 14 Drawing Figures

FIG. 6C
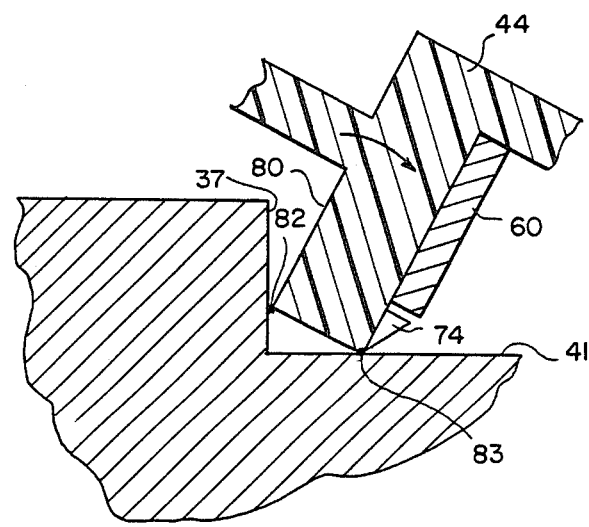
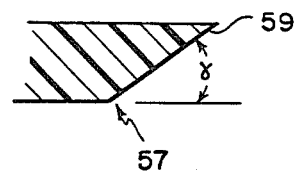
FIG. 8

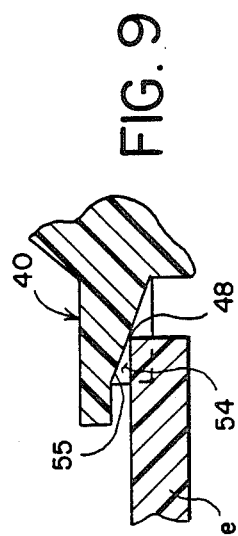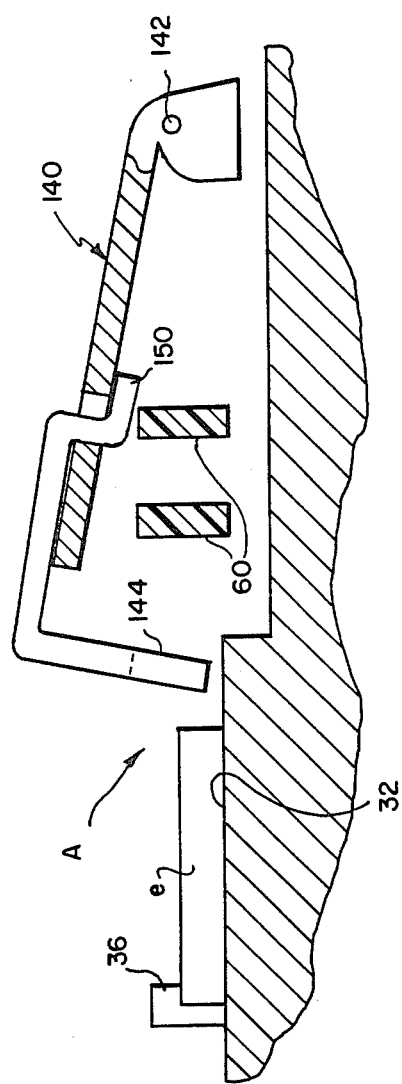

SIMPLIFIED TEST ELEMENT ADVANCING MECHANISM HAVING POSITIVE ENGAGEMENT WITH ELEMENT

FIELD OF THE INVENTION

This invention relates generally to an analyzer used to detect densities as a measure of analyte concentration in biological liquids. More specifically, it relates to a simplified mechanism in such an analyzer and a method for advancing test elements through the stations of such an analyzer.

BACKGROUND OF THE INVENTION

Conventionally, a variety of reciprocating linear drive means have been provided for large, automated clinical analyzers. Generally, these involve pushers or pullers that engage a test element for movement along a generally horizontal support surface, called a "track", from underneath or above, that support surface. Examples are shown in U.S. Pat. Nos. 4,152,390, issued May 1, 1979; and 4,219,529, issued Aug. 26, 1980.

Although generally effective for their intended use, such mechanisms are generally large and expensive. Furthermore, they have other disadvantages: a claw mechanism that protrudes upwardly from underneath can upset a test element if the claw projections are not accurately aligned with the element's edges. A claw protruding downwardly from above does not have this disadvantage, but it does tend to occupy the space within the track. As a result, access to the track, such as to clear a test element jam, is difficult to obtain. This has not been a serious difficulty in large analyzers serviced by highly skilled personnel. However, in a simpler machine located in a doctor's office, the users are generally not skilled enough for such disassembly. Thus, when smaller analyzers were designed for the doctor's office, in the interest of simplicity, the linear advancing mechanisms have been a simple pusher blade that is either manually operated, or directly driven by a simple motor connection. Examples of both appear in, e.g., U.S. Pat. No. 4,424,191. Such simple blades, although effective, lack a positive engagement with the test element—that is, there are no provisions for positively gripping the test element. For this reason, the advancing mechanisms of such smaller analyzers lack the ability within the pusher blade itself to control the sideways location of test elements on the generally horizontal support surface.

What has been desired prior to this invention is an advancing mechanism that is not as cumbersome as those used in the larger analyzers, but which provides positive sideways control of the test element within the portion that contacts the element for movement.

SUMMARY OF THE INVENTION

The present invention features an advancing mechanism for test elements which, though simplified in construction, provides a positive engagement of the test element that controls sideways movement of the test elements.

More specifically, in accord with one aspect of the invention there is provided a test element mover for sliding test elements along a support surface in a predetermined direction. The mover comprises a body portion constructed to mount the mover onto a reciprocating moving means, engaging means projecting from one side of the body portion for engaging such test elements, the engaging means being constructed to engage a side edge of a test element, and a pivot lever arm extending from the side of the body portion that is opposite to the one side, constructed to cause, when pushed, the mover to pivot about an axis that is substantially parallel to the test element side edge.

In accord with another aspect of the invention, there is provided a test element advancing mechanism for use in an analyzer to move such test elements from station to station. The mechanism comprises (a) a support surface over which such elements are slidably advanced in a predetermined direction, (b) a test element mover, the mover including means projecting therefrom for engaging such test elements, (c) means for reciprocating the mover along a surface disposed to one side of the support surface, a portion of the mover being constructed to engage the mounting means, and (d) means for pivoting the mover about an axis that extends parallel to the predetermined direction, so that the engaging means are moved into or out of contact with such test elements, the mover including a lever arm emanating from one side of the reciprocating means engaging portion and constructed to interact with the pivoting means, the test element engaging means of the mover emanating from the side of the reciprocating means engaging portion opposite to the one side.

In accord with yet another aspect of the invention, there is provided a method for advancing test elements through various stations.

Thus, it is an advantageous feature of the invention that a simplified advancing mechanism is provided for test elements without sacrificing the ability to control sideways movement of the advancing element.

It is a related advantageous feature of the invention that the advancing mechanism leaves the track over which the test elements are advanced, freely accessible for maintenance without sacrificing control of the advancing test element.

Other advantageous features will become apparent upon reference to the following Description of the Preferred Embodiments, when read in light of the attached drawings.

BRIEF DESCRIPTION OF THE DRAWINGS

FIG. 6C is an enlarged fragmentary sectional view taken from FIG. 6B;

FIG. 8 is a fragmentary sectional view taken generally along the line VIII—VIII of FIG. 3;

FIG. 9 is a fragmentary sectional view further illustrating the engagement of a test element with the test element mover; and FIG. 10 is a fragmentary sectional view of the pivotable stop at station A.

DESCRIPTION OF THE PREFERRED EMBODIMENTS

The subject invention is described in connection with a preferred analyzer of simplified construction, such as is useful in a doctor's office. It is also described in connection with preferred test elements. In addition, it is applicable to any analyzer, regardless where used, and regardless of the type of test element being processed.

Preferred test elements are constructed to receive a liquid containing analyte and to produce a change detectable by reflected light. Most preferred are multizoned elements having a plurality of reagents and/or functions that are divided among layered zones. Highly preferred are elements in which the zones are separate but contiguous layers, for example, a multi-layered test element as described in U.S. Pat. No. 3,992,158, issued on Nov. 16, 1976, or in U.S. Pat. No. 4,258,001, issued on Mar. 24, 1981. The test elements of said patents include an uppermost layer that functions to transport the liquid to be tested to the next adjacent layer or layers. Such uppermost layer optionally includes a reagent for the test, for example, one or more enzymes operative upon the analyte of choice. The next adjacent layer or layers preferably include a matrix and binder and remaining reagents for the assay. These remaining reagents include those necessary to produce a detectable signal in increasing or decreasing amounts, e.g., a change in reflection density in response to the reaction of the analyte. Most preferably, such layers are formed to provide an integral element, within a support frame apertured to receive a liquid drop on the uppermost layer, as described for example, in U.S. Pat. No. 4,169,751, issued on Oct. 2, 1979. (The terms "upper", "lower" and similar directional terms are used herein with respect to orientations of parts during their actual use.)

Figure 1:
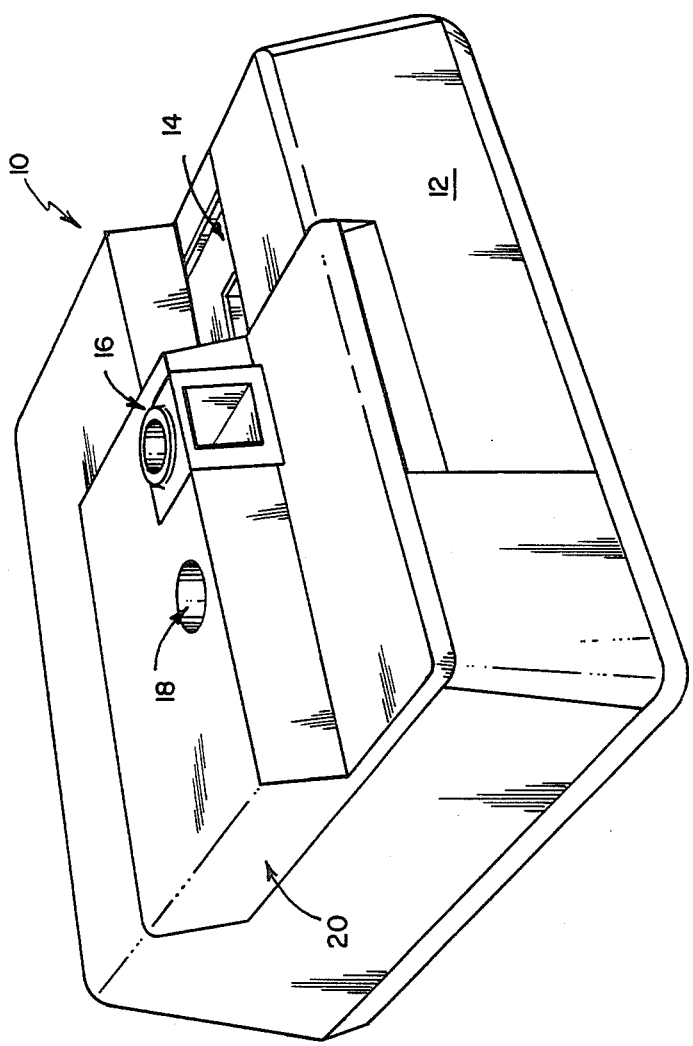
FIG. 1 is a perspective view of an analyzer constructed in accordance with the invention.

An analyzer 10 constructed in accordance with the invention comprises, FIG. 1, a frame 12, a manually actuated loading station 14, a patient sampledispensing station 16, an optional wash station 18, and other stations interior of the cover 20 of the analyzer. It also includes conventional microprocessors and output devices, not shown, which are not part of this invention. Station 16 provides mechanical support for a dispensing pipette, not shown.

Figure 2:
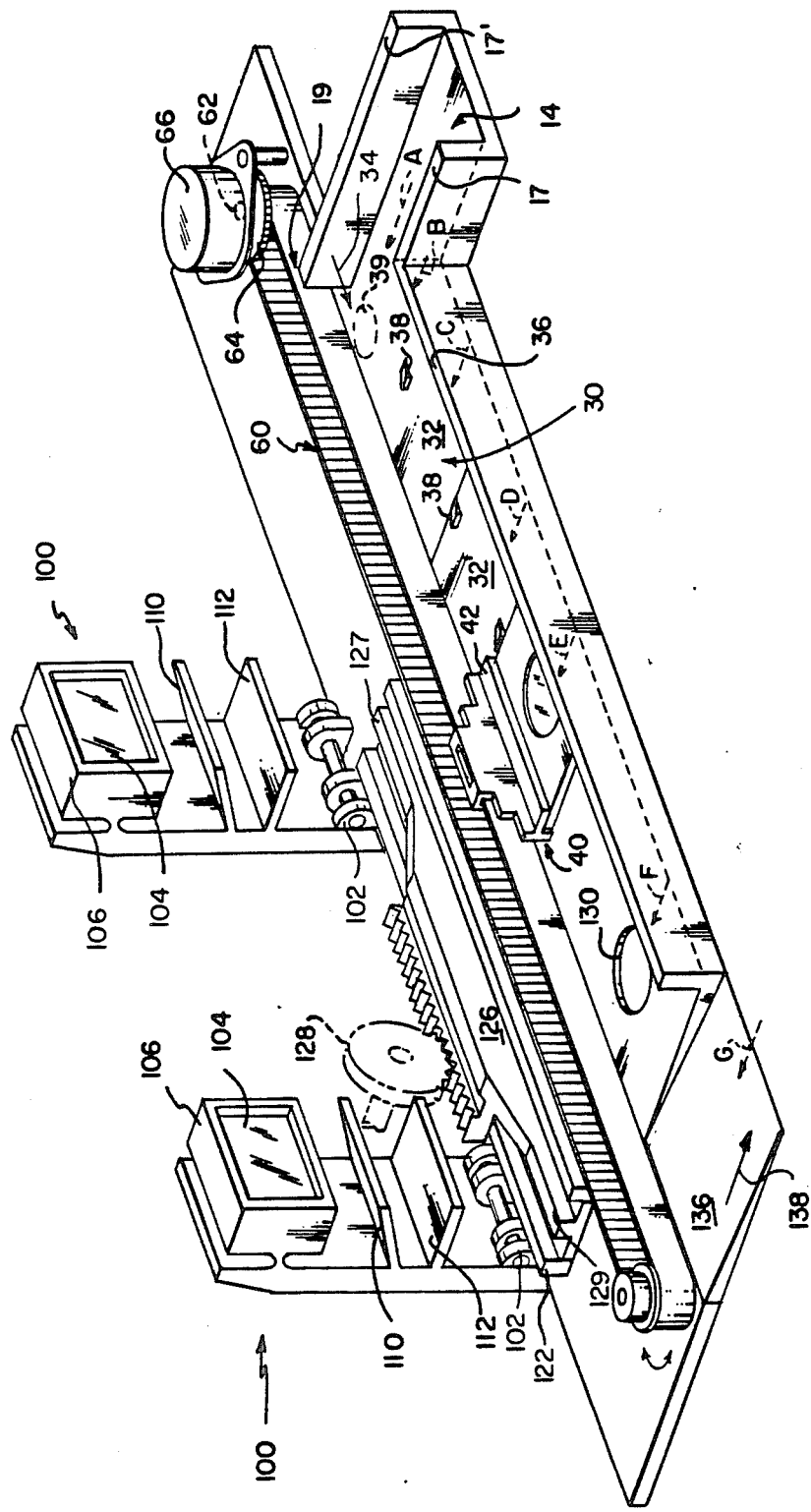
FIG. 2 is an isometric view of the test-element advancing mechanism of the invention used in the analyzer, the pivotable cover arms having been raised for clarity and the pivotable stop having been omitted.

The advancing mechanism of the invention is better understood by reference to FIG. 2. The loading station 14 is a manual loading station whose sole function is to allow the operator to push a test element onto a generally horizontal support surface 32 of track 30 over which the element "e" is advanced by the invention. The loading station incorporates two sidewalls walls 17 and 17' that guide elements "e" to track 30. Sidewall 17' does not extend across the entire width of track 30, but leaves an opening 19 that accommodates the mover of the invention, as discussed hereinafter. Track 30 extends in a linear direction consistent with the direction 34 that the test elements "e" are to advance. The first station A on track 30 features a conventional bar code reader, shown schematically at 39, and a pivotable stop 140, shown in FIG. 10 only, for clarity. The next station B downstream of station A is a hold station. Station C thereafter is the sample dispensing station that coincides with station 16 in cover 20, FIG. 1. Station D, FIG. 2, is a preheat station, and portion 32' of track 32 is a heat-conducting platen heated by buried heaters, not shown. Station E coincides with the optional wash station 18, FIG. 1. A wash fluid is added at this station through the use of a pipette, not shown. Station F is the read station, and station G is the unloading station.

Figure 6A:
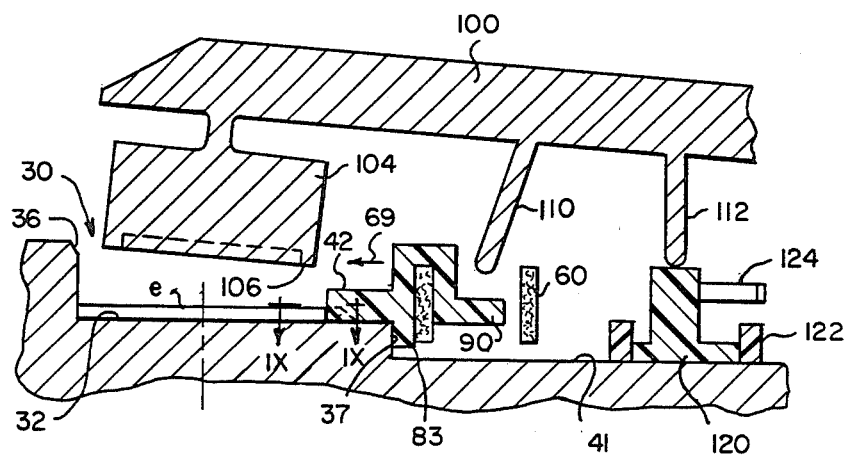
FIG. 6A and 6B are fragmentary sectional views illustrating the cooperation between the cover arms and the mover so as to cause the pivoting of the latter away from the test element.
Figure 6B:
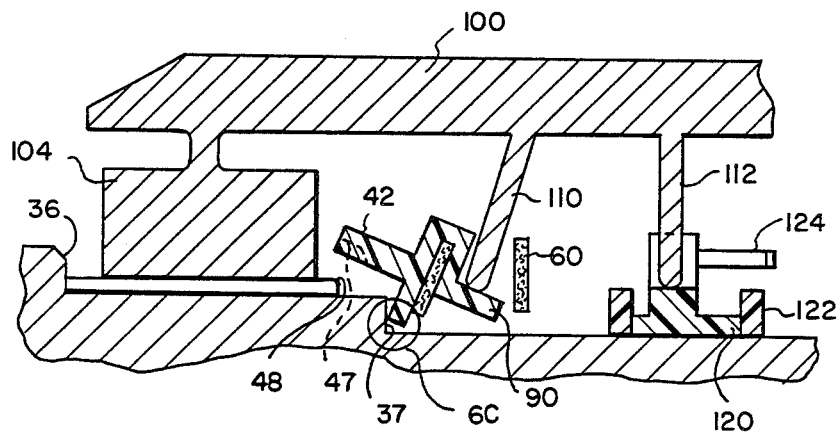

A ridge 36 is provided alongside of, and parallel to, support surface 32, as also seen in FIGS. 6A and 6B, projecting above that surface. As will become apparent, this surface is a reference surface for limiting sideways movement of the elements "e", that is, movement orthogonal to direction 34.

A step 37 is provided on the opposite side of surface 32 from ridge 36. The step terminates in a floor 41, FIG. 6A. The surface of step 37 is the bearing surface for the mover, as is further described hereinafter.

Behind each station, restraining bumps 38 are preferably provided, either in surface 32 or 32', or optionally in ridge 36, FIG. 2. These bumps 38 are ramped so as to provide minimal sliding resistance to an element "e" in direction 34, but block movement of such elements in the opposite direction. Optionally, bumps 38 can be spring-biased so as to retract when test elements slide thereover in the advancing direction 34. To keep the test elements from tipping, preferably bumps 38 are located close to ridge 36.

In accord with one aspect of the invention, a mover 40 is provided to positively engage a test element "e" during its movement along track 30. Mover 40 is secured to a reciprocating means 60, which is shown as an endless belt driven by a drive shaft 62, a gear 64, and a conventional stepper motor 66 engaging gear 64 by its own gear, not shown. An idler gear 68 is located relative to shaft 62 so that belt 60 moves parallel to track 30 for most of its movement. Any reciprocating, flexible endless member is useful as means 60, for example, a chain drive to which mover 40 is bolted. Alternatively, mover 40 can be formed as an integral part of belt 60.

Belt 60 is preferably flexible, for the reason that it allows the test element mover to accommodate test elements that might be slightly larger than the nominal size, due to tolerance factors. It is further flexible so that mover 40 can be biased in the direction of arrow 69 as shown in FIG. 6A, by the location of belt 60, so that mover 40 rides along surface 37.

Figure 3:
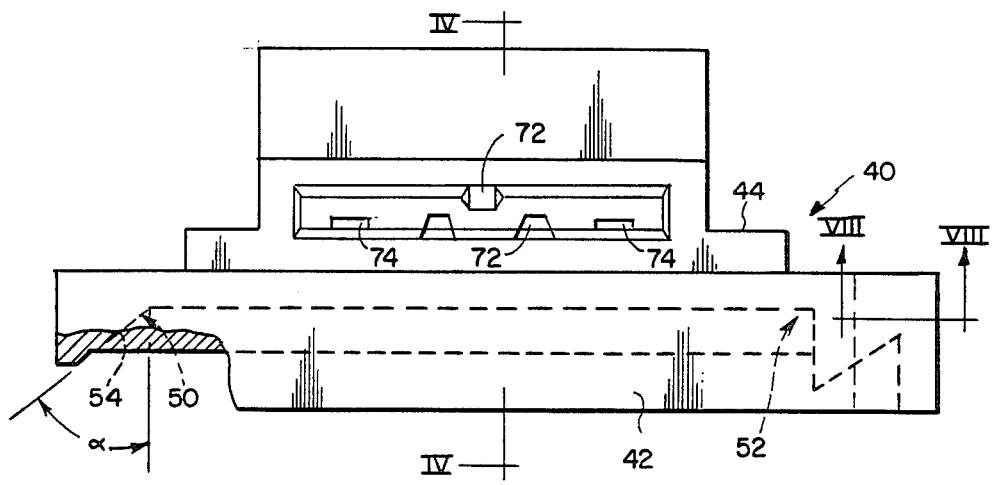
FIG. 3 is a partially broken away plan view of the mover shown in FIG. 2.
Figure 4:
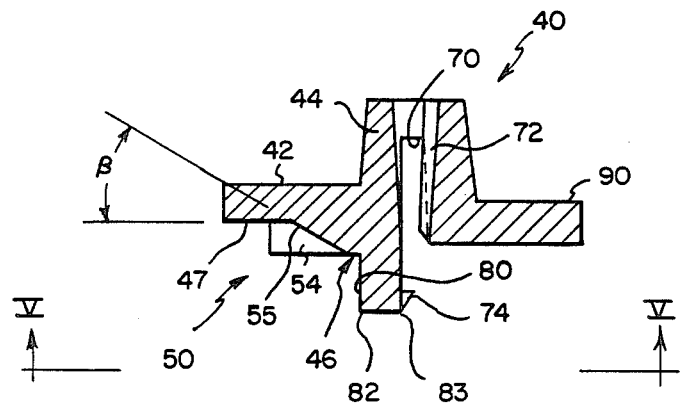
FIG. 4 is a section view taken generally along the line IV—IV of FIG. 3.
Figure 5:
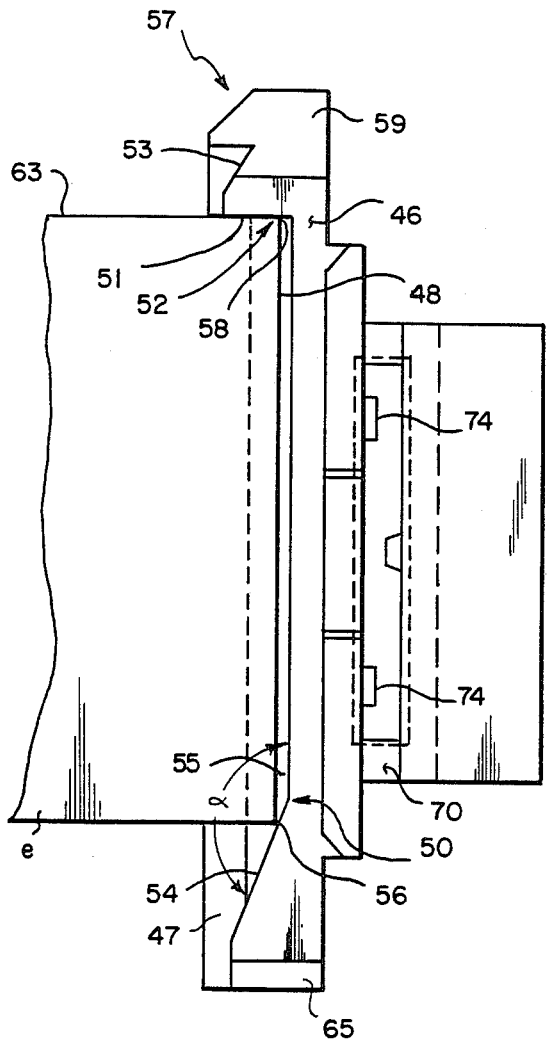
FIG. 5 is a fragmentary bottom view of the mover, particularly as seen along the line V—V of FIG. 4, and part of a test element engaged by the mover.

As is more readily apparent in FIGS. 3 and 4, mover 40 is constructed with means for positively engaging the test elements "e." Such means include a lip 42 projecting outwardly over track 30 from the main body 44 of the mover. The undersurface 46 of lip 42, FIGS. 4 and 9, is especially constructed to cause the mover to engage the side edge 48 of each test element "e". More specifically, undersurface 46 is undercut at 47 and 55, FIG. 4, to accommodate a test element "e" underneath, FIG. 9. In addition, two interior corners 50 and 52, FIG. 5, are provided in such undersurface, spaced apart the length of side edge 48 of a test element "e". Corner 50 is provided with a vertical (when used) surface 54, forming an angle α, FIGS. 3 and 5, sufficient to allow corner 50 to disengage the respective exterior corner 56, of element "e", at the top surface of the element, by pivoting away, arrow 61, from engagement with that corner, FIG. 7C. The angle α of surface 54 can be between about 150 and about 170 degrees, and most preferably is about 160°. Less than 150° is useful so long as the resultant force on the test element is to the rail side of bumps 38, as would be the case if bumps 38 are located closer to step 37 than to ridge 36. Such force direction is preferred to keep the test element from tipping.

Surface 55, FIG. 4, of undersurface 46 is beveled to ensure proper engagement of side edge 48 of the test element, as described hereinafter. Angle $\beta$ can be between about 20 and about 70 degrees, and is most preferably 30°.

In contrast, corner 52 is squared off at 90°, FIG. 5 and FIGS. 7A-7C, so that corner 52 and surface 51 thereof will not disengage with the trailing surface 58 of element "e" as the two are engaged. It is corner 52 and specifically surface 51 that transmit the driving force from mover 50 to element "e" in direction 34.

End 57, FIG. 5, of mover 40 adjacent to corner 52, is beveled at surface 59, at an angle $\gamma$, FIG. 8. $\gamma$ is between about 30° and about 60°, and most preferably is about 45°. Optionally, FIG. 5, end 57 is further chamfered at 53 to extend undercut 47 out closer to the end 57. The purpose of both surfaces 59 and 53 is to allow mover 40 to readily move up over a test element "e" in a station upstream from the previous position of mover 40, when the latter is withdrawn to that upstream station. Additional surface 53 is preferred if there are track obstacles that render mover 40's upward pivoting restricted at any location. Similarly, the opposite end of mover 40 is beveled at surface 65, preferably at angle $\gamma$, to facilitate movement of mover 40 over a test element at a downstream station.

Body 44 of mover 40 is notched at 70, FIG. 4, to receive and engage belt 60. One or more opposing teeth 72 assist in locking the belt within the notch.

Teeth 74 at the bottom of notch 70 assist in keeping mover 40 on the belt.

Side surface 80 of mover body 44 provides the surface that bears on step 37 of the analyzer during the mover's reciprocation. The reciprocation occurs, FIG. 6A, to one side of, and parallel to, track 30 and the linear direction 34 of movement along the track. Side surface 80 is also used to allow the mover to pivot out of engagement with elements "e." More specifically, FIG. 6C, corner 82 of surface 80 is the primary pivot axis of the mover, and it generally bears against, and extends parallel to, reciprocation surface 37, FIG. 4 and FIG. 6B. Thus pivot axis 82 extends parallel to track 30, to one side thereof.

A secondary pivot can also occur at corner 83 of body portion 44, when it encounters floor 41. Alternatively, pivoting about corner 83 is dispensed with by lowering floor 41 in relation to corners 82 and 83 (not shown).

To allow mover 40 to be pivoted about axis 82, a lever arm 90 projects from body 44 from the side of body 44 that is opposite to the side from which lip 42 projects, FIG. 4 and FIGS. 6A and 6B. The extent of the projection of arm 90 is sufficient to allow the mover to be engaged by a pivot ridge of a cover arm, described hereinafter.

At station D and F, best results are obtained if elements "e" are covered while at the stations. Such covering acts to prevent evaporation of the liquid sample, and to ensure uniform heating if the cover is also heated. To that end, cover arms 100 are journaled at 102 to the frame of the analyzer, FIG. 2, in a position that allows them to cover a test element "e" at either station. Such arms comprise a cover head 104 projecting from the underside of arm 100, that includes a sealing edge 106 that approximates a seal around the appropriate part of the top of an element "e", as is also shown in FIG. 6A. In addition, head 104 comprises a heat-conductive material and a heating element (not shown) to maintain the temperature at a value slightly greater than that of track 30, to prevent condensation onto the head. Also projecting from the underside of the arm are a pivot ridge 110 and a cam follower 112. Ridge 110 is positioned to bear on lever arm 90 of mover 40 if arm 100 is lowered to contact element "e", FIGS. 6A and 6B.

To raise and lower arm 100 so that an element "e" can be moved into position thereunder, a cam 120 is mounted for reciprocation within a track 122, FIGS. 2, 6A and 6B. The camming surface is camming shoulder 126, disposed between two low surfaces 127 and 129. A rack gear 124 projects from the camming shoulder 126 of cam 120, to engage a gear 128 driven by a stepper motor, not shown.

To make a reading at station F, FIG. 2, a suitable reflectometer is disposed under support surface 32'. Any reflectometer adapted to make the desired reading can be used. Window 130 allows the reflectometer access to an element "e" disposed at station F. Most preferably, heating platen 32' extends over into stations E and F.

The final station G features a chute 136 inclined to allow a test element "e" to unload itself from mover 40, and to discharge out of the apparatus in the direction of arrow 138.

The sequencing of mover 40 between stations A–G is preferably handled by a conventional microprocessor, not shown, programmed in a conventional manner.

Most preferably, an arm 140 is fixed at 142 to the analyzer at station A, FIG. 10, to keep test element "e" from being pushed up against belt 60. The arm includes a pivotable portion 144 that pivots upwardly as mover 40 cams into it. That is, the surface of portion 144 is slanted to act as the camming surface against which mover 40 cams upwardly to force portion 144 to rise out of the way of mover 40. A tail piece 150 allows portion 144 to pivot upwardly only, relative to fixed arm 140.

Thus, the method of moving the test element through the analyzer comprises the steps of (a) engaging one of the side edges of the test element at a first station with a test element mover positioned to one side of the test element that corresponds to said side edge, (b) pushing the test element from the first station in a direction parallel to the side edge to a subsequent station, using the mover, (c) holding the test element stationary at such subsequent station while disengaging the mover, (d) engaging another such test element at its side edge at the first station, (e) and moving the test elements to an unloading station using the mover.

The operation of the apparatus will be apparent from the preceding description. In summary, FIGS. 2, 6A-6B and 7A-7C, an element "e" is pushed onto track 30 and support surface 32, at station A. If mover 40 is not already at this surface, motor 66 is activated to pull belt 60 and mover 40 back to station A. Stop 140 pivots out of the way as mover 40 is pulled into station A. The construction of undersurface 46 with its overhang allows mover 40 to ride up over the element. Opening 19 accommodates mover 40 so that corner 52 can engage corner 58 of element "e", FIG. 7A. Thereafter, belt 60, mover 40, and element "e" are moved to the left, through station B and then to the sample dispensing station C, where sample is dispensed. During all such advancing of element "e", surfaces 54 and 55 of mover 40 act to push and engage side edge 48 of element "e" towards reference ridge 36, FIGS. 5, 6A, 7B and 9, thereby accurately locating the elements in a sideways direction. Thus, mover 40 contacts element "e" at corner 56 with surface 54, and along side edge 48 with surface 55. In addition, trailing edge surface 63 of element "e" is engaged by interior corner 52, particularly along trailing surface 51 of such corner, FIG. 5. Thereafter, FIG. 7B, the element is moved again in direction 34 to station D, the preheat station. At this and other stations, accurate location of element "e" lengthwise along the direction of arrow 34 is achieved by first pulling element "e" up and over restraining bump 38, FIG. 7B, and then retracting the advance of mover 40 and element "e" a slight amount until the element contacts bump 38 and prevents further retrograde motion, FIG. 7C. At this point, element "e" is centered for the operation appropriate at that station.

Figure 7A:
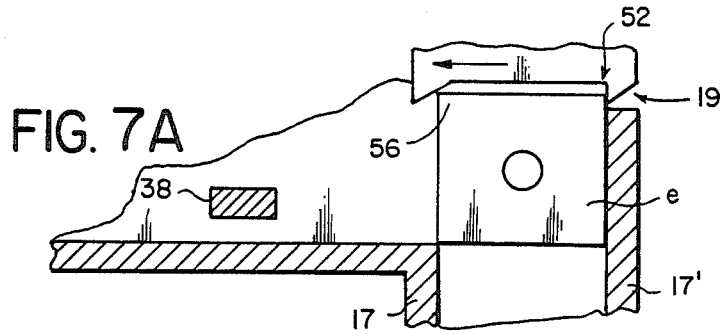
FIGS. 7A–7C are fragmentary, generally schematic, plan views illustrating part of the operation of the mechanism.
Figure 7B:
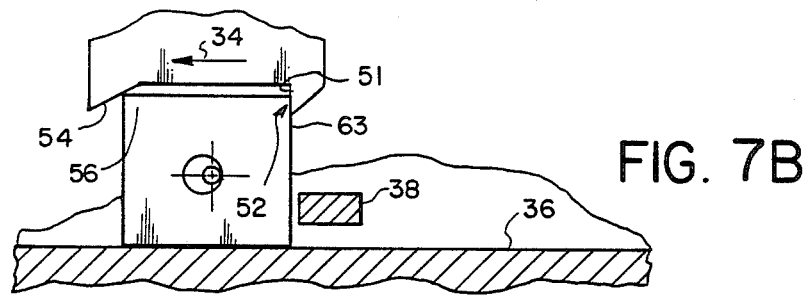
Figure 7C:
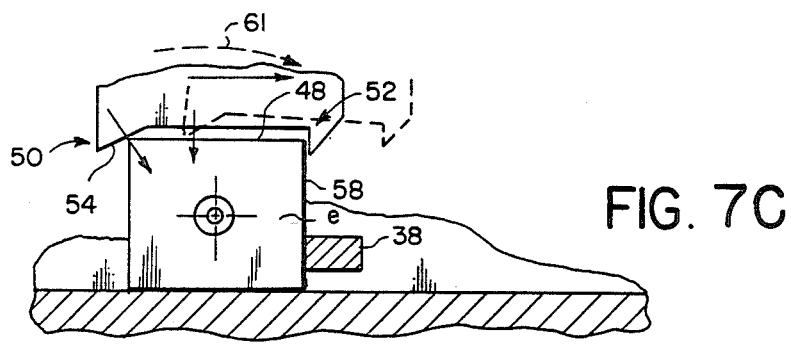
Figure 2:
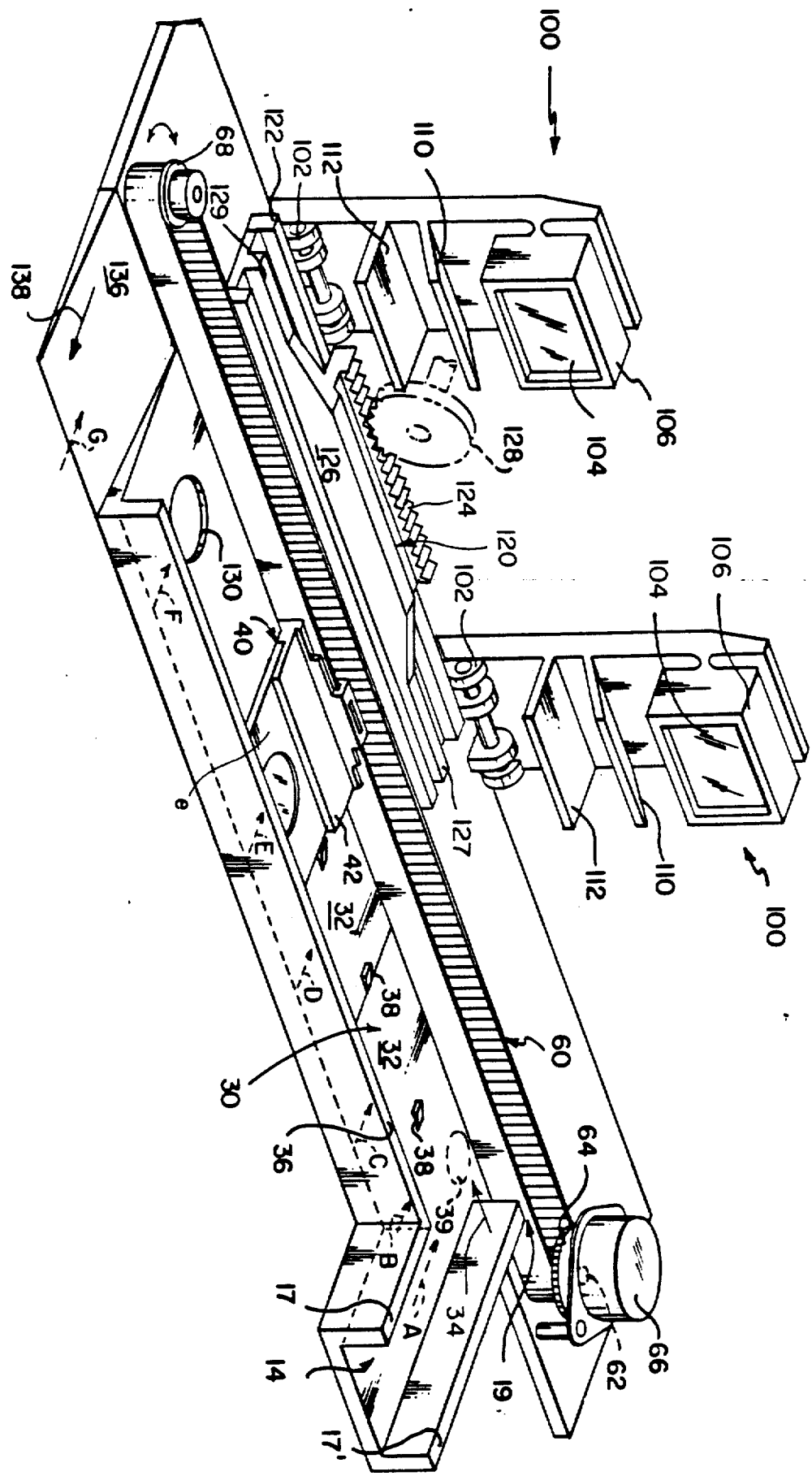

In the event it is desired to leave element "e" at a station and withdraw mover 40 to a retrograde position to engage another test element, this is readily accomplished due to surface 54 allowing such disengagement. The phantom position of mover 40, FIG. 7C, illustrates the manner in which mover 40 pivots corner 50 out away from corner 56 of element "e."

If element "e" is at station D, mover 40 can be advanced as well, without pulling such an element prematurely out of that station. This is possible since, once an element enters station D (and F as well), cam 120 is translated so that cam followers 112 ride on the low points 127 or 129 of the cam, and cover 104 drops into contact with the slide. At the same time, FIGS. 6A and 6B, ridge 110 pushes against lever arm 90 of mover 40, causing the mover to pivot about the axis coinciding with edge 82, out of engagement with the test element. When it is necessary to move an element "e" into or out of station D (or F), cam 120 is translated so that shoulder 126 pushes up the cam follower 112, and thus head 104. Shoulder 126 optionally has enough extension in the direction of arrow 34 that the cam followers of both arms can be raised simultaneously.

Optionally, pivot ridge 110 can be omitted from arm 100 at station F, but only if head 106 exerts a sufficient downward thrust on element "e" as to allow mover 40 to slidably disengage while moving in a retrograde fashion to a previous station.

The invention has been described in detail with particular reference to preferred embodiments thereof, but it will be understood that variations and modifications can be effected within the spirit and scope of the invention.

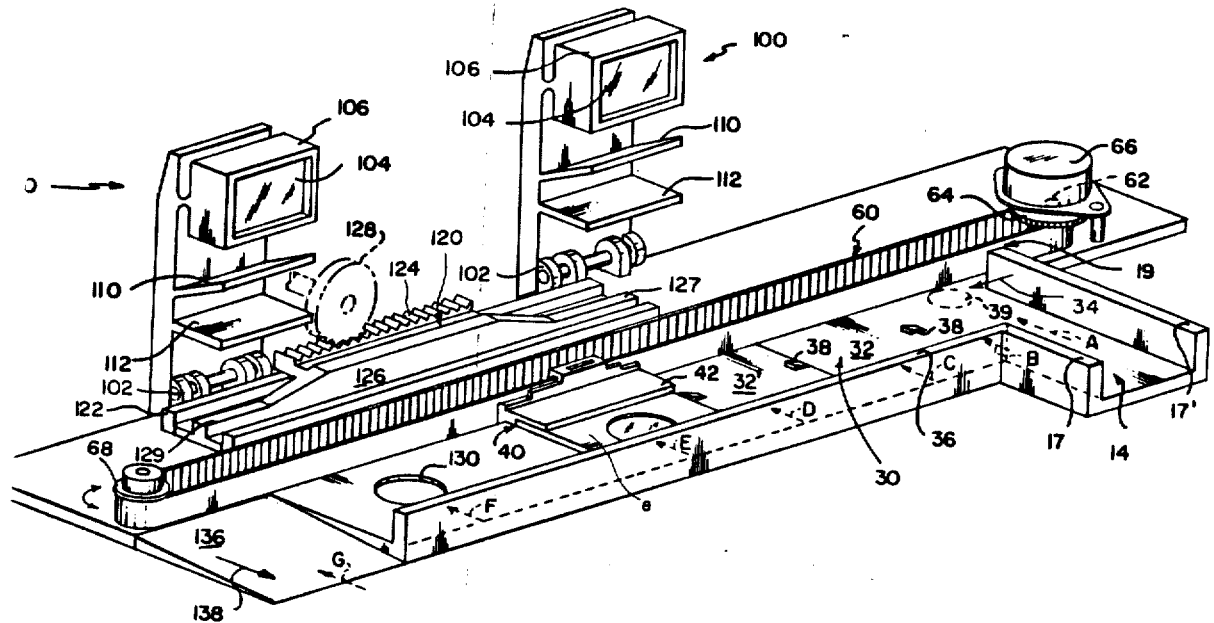

What is claimed is:

1. A test element advancing mechanism for use in an analyzer to move a test element from station to station, the mechanism comprising
   (a) a support surface over which elements are slidably advanced in a predetermined direction, said surface having first and second edges,
   (b) a test element mover having a pivot axis extending parallel to said support surface, said mover including engaging means projecting therefrom for engaging test elements, said test element engaging means including two interior corners and a surface between them constructed to engage at least one edge of engaged test elements along one side of such test elements, said one test element edge being an edge that extends generally parallel to said pivot axis,
   (c) means for reciprocating said mover along a surface disposed to one side of said support surface, a portion of said mover being constructed to engage said reciprocating means, and
   (d) means for pivoting said mover about said axis, so that said engaging means are moved into or out of contact with test elements, said mover including a lever arm emanating from one side of said reciprocating means engaging portion and constructed to interact with said pivoting means, said reciprocating means being sufficiently flexible as to be rotatable about said pivot axis when said pivoting means is activated,
   said test element engaging means of said mover emanating from a side of said reciprocating means engaging portion that is opposite to said one side,
   whereby said mover engages test elements at a side edge.

2. An advancing mechanism as defined in claim 1, and further including a reference surface connected at an edge thereof to one of said edges of said support surface, whereby said mover pushes an engaged test element sideways against said reference surface to positively locate such test element sideways along said support surface.

3. An advancng mechanism as defined in claim 1, wherein said interior corners engage opposite sides of test elements that are perpendicular to said pivot axis.

4. An advancing mechanism as defined in claim 1, wherein one of said interior corners leads the other when said mover advances in said predetermined direction, the leading one of said interior corners is shaped to allow said leading corner to pivot out of engagement with the corresponding one of said interior corners is provided with a 90° angle to preclude disengagement of said trailing corner with the corresponding exterior trailing corner of a test element, except when said mover is pivoted about said axis.

5. An advancing mechanism as defined in claim 4, wherein said leading corner forms an angle that is at least 150°.

6. A test element mover for sliding test elements along a support surface in a predetermined direction, said mover comprising
   a body portion constructed to mount the mover onto a reciprocatable moving means, said portion having two opposite sides,
   engaging means projecting from one of said sides of said body portion for engaging a side edge of a test element, and comprising two interior corners and a surface between them constructed to engage said edge of a test element,
   and a pivot lever arm extending from the other of said sides of said body portion, constructed to cause, when pushed, said mover to pivot about an axis that is substantially parallel to a test element side edge.

7. A test element mover as defined in claim 6, wherein said interior corners engage opposite sides of test elements that are perpendicular to said pivot axis.

8. A test element mover as defined in claim 6, wherein one of said interior corners leads the other when said body portion advances in said predetermined direction, the leading one of said interior corners is shaped to allow said leading corner to pivot out of engagement with the corresponding exterior corner of a test element, and the trailing one of said interior corners is provided with a 90° angle to preclude disengagement of said trailing corner with a corresponding exterior trailing corner of the test element, except when said mover is pivoted about said axis.

9. A test element mover as defined in claim 8, wherein said leading corner forms an angle that is at least 150°.

* * * * *

UNITED STATES PATENT AND TRADEMARK OFFICE
CERTIFICATE OF CORRECTION

PATENT NO. : 4,710,352            Page 1 of 3

DATED : December 1, 1987

INVENTOR(S) : Daniel A. Slater, William A. Meredith and Mark J. Devaney

It is certified that error appears in the above-identified patent and that said Letters Patent are hereby corrected as shown below:

Column 8, line 40 should read: --with the corresponding exterior corner of test elements, and the trailing--.

The drawing, Figure 2, should appear as in the attached, rather than as printed in the patent.

The Title Page should be deleted to appear as per attached Title Page.

Signed and Sealed this

Seventeenth Day of May, 1988

Attest:

DONALD J. QUIGG

Attesting Officer

Commissioner of Patents and Trademarks

United States Patent [19]

Slater et al.

[11] Patent Number: 4,710,352
[45] Date of Patent: Dec. 1, 1987

[54] SIMPLIFIED TEST ELEMENT ADVANCING MECHANISM HAVING POSITIVE ENGAGEMENT WITH ELEMENT

[75] Inventors: Daniel A. Slater; William A. Meredith; Mark J. Devaney, all of Rochester, N.Y.

[73] Assignee: Eastman Kodak Company, Rochester, N.Y.

[21] Appl. No.: 777,985

[22] Filed: Sep. 20, 1985

[51] Int. Cl.$^4$ .............................. G01N 35/00
[52] U.S. Cl. ........................ 422/63; 198/465.1; 198/748; 198/803.01; 422/65; 436/46
[58] Field of Search ............ 198/465.1, 465.2, 748, 198/803.01; 436/46, 47; 422/65, 67, 73, 63

[56] References Cited

U.S. PATENT DOCUMENTS

| | | | |
|---|---|---|---|
| 3,104,768 | 9/1963 | Bassett | 198/748 |
| 3,655,025 | 4/1972 | Wilkin | 198/748 |
| 3,708,264 | 1/1973 | Jottier | 422/65 |
| 4,152,390 | 5/1979 | Nosco et al. | 422/65 |
| 4,219,529 | 8/1980 | Tersteeg et al. | 422/65 |
| 4,269,803 | 5/1981 | Jessop | 422/65 |
| 4,378,872 | 4/1983 | Brown | 198/748 |
| 4,424,191 | 1/1984 | Jakubowicz | 422/65 |
| 4,430,299 | 2/1984 | Horne | 422/67 |

FOREIGN PATENT DOCUMENTS 55-71951  5/1980  Japan ........................ 422/65

Primary Examiner—Michael S. Marcus
Attorney, Agent, or Firm—Dana M. Schmidt

[57] ABSTRACT

There is disclosed a test element advancing mechanism for use in an analyzer to move such test element from station to station, and a method of doing the same. The mechanism features a support surface over which the test elements move in a predetermined direction, a test element mover for engaging and moving the test elements, means for reciprocating the mover along a surface disposed to one side of the support surface, a portion of said mover being constructed to engage the reciprocating means, and means for pivoting the mover about an axis that extends parallel to the movement direction so that the engaging means are moved into or out of contact with such test elements. The test element mover includes a lever arm emanating from one side of the reciprocating means engaging portion, constructed to interact with the pivoting means. The mover also includes test element engaging means projecting from a side of the reciprocating means engaging portion that is opposite to the side from which projects the lever arm of the mover, for engaging the test elements.

9 Claims, 14 Drawing Figures